United States Patent
Bratkovski et al.

(10) Patent No.: US 8,582,097 B2
(45) Date of Patent: Nov. 12, 2013

(54) PHASE DETECTION OF RAMAN SCATTERED LIGHT

(75) Inventors: Alexandre M. Bratkovski, Mountain View, CA (US); Igor Lukyanchuk, Caix (FR)

(73) Assignee: Hewlett-Packard Development Company, L.P., Houston, TX (US)

( * ) Notice: Subject to any disclaimer, the term of this patent is extended or adjusted under 35 U.S.C. 154(b) by 344 days.

(21) Appl. No.: 13/016,395

(22) Filed: Jan. 28, 2011

(65) Prior Publication Data

US 2012/0194812 A1  Aug. 2, 2012

(51) Int. Cl.
 *G01J 3/44* (2006.01)
(52) U.S. Cl.
 USPC ............................... 356/301; 356/453
(58) Field of Classification Search
 USPC .................... 356/301, 322, 451, 453
 See application file for complete search history.

(56) References Cited

U.S. PATENT DOCUMENTS

| | | | |
|---|---|---|---|
| 5,247,343 A | | 9/1993 | Burch |
| 5,418,797 A | * | 5/1995 | Bashkansky et al. ............. 372/3 |
| 6,124,928 A | * | 9/2000 | Slater .............................. 356/317 |
| 7,361,501 B2 | | 4/2008 | Koo et al. |
| 7,495,823 B2 | | 2/2009 | Kanner et al. |
| 2006/0066848 A1 | * | 3/2006 | Frankel ......................... 356/301 |
| 2008/0304061 A1 | | 12/2008 | Ossikovski et al. |
| 2010/0067005 A1 | | 3/2010 | Davis et al. |

* cited by examiner

*Primary Examiner* — Tarifur Chowdhury
*Assistant Examiner* — Jonathan Hansen

(57) ABSTRACT

An apparatus for phase detection of Raman scattered light emitted from a sample includes a first polarizer positioned along a first optical path containing a first beam and a second polarizer positioned along a second optical path containing a second beam. The first polarizer and second polarizer polarize the first beam and the second beam in one of mutually perpendicular and mutually parallel first and second directions. The apparatus also includes an optical phase modulator positioned along the second optical path to controllably modulate a phase of the second beam, a beam splitter positioned to join the first beam and the second beam together, and a spectrometer to receive the joined first beam and second beam and to measure a phase shift of the first beam and the second beam.

15 Claims, 5 Drawing Sheets

PHASE DETECTION OF RAMAN SCATTERED LIGHT

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (for instance, visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman-scattering.

Raman-scattering optical spectroscopy employs an emission spectrum or spectral components thereof produced by inelastic scattering of photons by an internal structure of the material being illuminated. These spectral components contained in a response signal (for instance, a Raman signal) may facilitate determination of the material characteristics of an analyte species including identification of the analyte.

Unfortunately, the Raman signal produced by Raman-scattering is extremely weak in many instances compared to elastic or Rayleigh scattering from an analyte species. The Raman signal level or strength may be significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1:
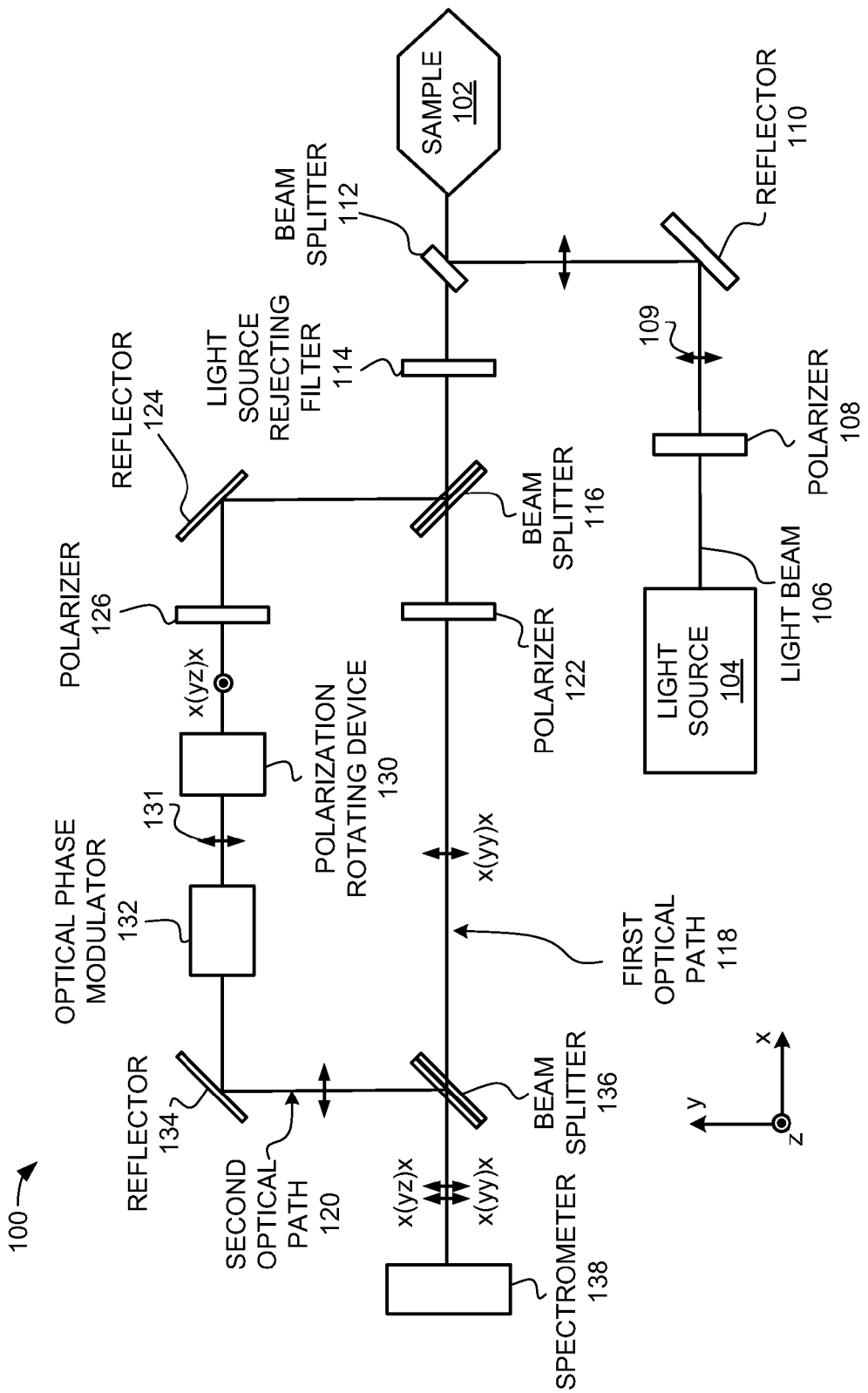
FIG. 1 shows a block diagram of an apparatus for phase detection of Raman scattered light emitted from a sample, according to an example of the present disclosure.

For simplicity and illustrative purposes, the present disclosure is described by referring mainly to examples thereof. In the following description, numerous specific details are set forth in order to provide a thorough understanding of the present disclosure. It will be readily apparent however, that the present disclosure may be practiced without limitation to these specific details. In other instances, some methods and structures are not described in detail so as not to unnecessarily obscure the description of the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on.

Disclosed herein are apparatuses and methods for phase detection of Raman scattered light emitted from a sample. The Raman scattered light may be defined by a tensor composed of a plurality of components, for instance, nine complex values, that define the amplitudes of the incident and scattered electromagnetic waves of the Raman scattered light. Conventional Raman spectroscopes merely measure the absolute values of the components forming the Raman tensor as a function of the frequency shift between incident and scattered waves at different scattering geometries, crystal orientations, and light polarizations. In contrast, the apparatuses and methods disclosed herein also enable the determination of the relative phases (signs) of the tensor components.

In one regard, the relative phases of the tensor components provide additional information that may be used in analyzing various aspects of the sample under consideration. For instance, the phase information may be used in determining the performance of surface enhancement mechanisms, for instance, to detect single molecules. By way of example, the phase information may enable a determination of whether a molecule is attached to a Raman-active material, such as, a nano-object, metallic ball, pits, etc. More particularly, the spectrum of vibration of the molecule is likely to change depending upon its attachment mechanism to the Raman-active material and the determination of the phases of the Raman tensor components as disclosed herein enable a determination of the changes in the spectrum of vibration.

As discussed in greater detail herein below, the Raman scattered light traverses a first optical path and a second optical path. As the first and second beams traverse the first and second optical paths, the first and second beams are polarized into various orientations during different iterations to enable shifts in the phases of the first and second beams to be determined for different combinations of orientations. In addition, an optical phase modulator/phase shifter (hereinafter referred to as "optical phase modulator"), which may include nonlinear optical fiber, Silicon-on-Insulator (SOI) waveguides, silicon metal-oxide-semiconductor capacitor, etc., is positioned along the second optical path to controllably vary the phase of the second beam along the second optical path and thereby control the phase shift of the second beam. As such, when the first beam and the second beam are combined, the relative phase of the combined beam may be determined since the phase of the second beam is known.

FIG. 1 shows a block diagram of an apparatus 100 for phase detection of Raman scattered light emitted from a sample, according to an example of the present disclosure. It should be understood that the apparatus 100 depicted in FIG. 1 may include additional components and that some of the components described herein may be removed and/or modified without departing from a scope of the apparatus 100. It should also be understood that the components depicted in FIG. 1 are not drawn to scale and thus, the components may have different relative sizes and positions with respect to each other than as shown therein.

Generally speaking, the apparatus 100 may comprise part of an apparatus for performing surface enhanced Raman spectroscopy (SERS). In this regard, the sample 102 may comprise an analyte that has been adsorbed on or positioned within a few nanometers of a Raman-active material. In addition, the apparatus 100 may be employed to detect single molecules of the sample 102 that have been attached to or otherwise positioned near the Raman-active material.

As shown in FIG. 1, the apparatus 100 includes a light source 104, such as, a laser beam source, that is to emit a light beam 106, such as, a laser beam, on the sample 102, in which the light beam 106 causes Raman light to be scattered from the sample 102 or, more particularly, a molecule of the sample 102. The light beam 106 is depicted as passing through a polarizer 108 that causes the light beam 106 to have a particular orientation as indicated by the arrow 109. The light beam 106 may be oriented in the particular orientation to enable the light from the light beam 106 to more easily be filtered out from the Raman scattered light from the sample 102.

Although the light beam 106 has been depicted as being redirected by a reflector 110 and a beam splitter 112 prior to illuminating the sample 102, it should be understood that either or both of the reflector 110 and the beam splitter 112 may be optional. It should also be understood that the apparatus 100 may include additional reflectors 110 or beam splitters 112 depending upon the originating location of the light beam 106 with respect to the sample 102.

The light beam 106 illuminating the sample 102 causes inelastic Raman scattering from the sample 102, or a molecule of the sample 102, which is enhanced by Raman-active material. The electromagnetic field in light beam 106 vibrates at a particular frequency ($f_0$) and the molecule in the sample 102 vibrates at another frequency ($f_1$), which is significantly smaller than the frequency of vibration of the light beam 106. For instance, the light beam 106 at visible light may vibrate at around (hv=2-2.5 electron volts (ev) in the visible range, while the vibrational frequency of the molecule may be around 0.2 ev (($hv_0$)≤0.2 ev) or much smaller. As such, the molecule has a relatively slow vibrational modulation, which modulates the Raman scattered light being emitted from the molecule.

The Raman scattered light being emitted from the molecule has a x component, a y component, and a z component. More particularly, the amplitudes of the incident ($E^{(i)}i$) and scattered ($E^{(s)}j$) electromagnetic waves of the Raman scattered light are related by virtue of the Raman tensor (Rij). In other words, $$E^{(i)}i = Rij\, E^{(s)}j.\qquad \text{Equation 1}$$

(i,j=x,y,z, and here summation goes over index j)
where Rij is the Raman tensor, i,j=(x,y,z) mark Cartesian coordinates, so that it relates Cartesian components of incident laser light and inelastically scattered Raman light (Raman photons) with frequency slightly shifted compared to the incident light.

According to an example, and as discussed in greater detail below, the Raman tensor (Rij) may comprise phases and absolute values. In this regard, for instance, the Raman tensor (Rij) may include nine complex values.

$$Rij = \begin{bmatrix} Rxx & Rxy & Rxz \\ Ryx & Ryy & Ryz \\ Rzx & Rzy & Rzz \end{bmatrix}\qquad \text{Equation 2}$$

In one regard, a Raman spectroscope may measure the absolute values of the elements of the Raman tensor (Rij) as a function of frequency shift between incident and scattered waves at different scattering geometries, crystal orientations, and light polarizations. If, for instance, a monochromatic light is reflected from a crystal surface along the same x-direction (back-scattering in the 180° xx-geometry of apparatus 100), the combination of the y- and z-orientations of the in- and out-come polarizers permits measurements of the Ryy, Rzz, and Rzy matrix elements of the Raman tensor Rij. The corresponding configurations are denoted as x(yy)x, x(zz)x and x(zy)x. In the 90° xy-scattering geometry of apparatus 200 (FIG. 2), the Ryx, Rzx, Rzz and Ryz components are measured by the variation of the y- and z-orientations of the incoming polarizer and the x- and z-orientation of the outcome polarizer (configurations x(yx)y, x(zx)y, x(zz)y and x(yz)y).

As described in detail herein, the apparatus 100 permits the simultaneous measurement of the absolute values of the Raman tensor components and their relative phases (signs). This information may be employed in determining whether the analyzed light has been emitted from a molecule of the target sample 102 in a relatively accurate manner. More particularly, for instance, the apparatus 100 may provide information on anchoring mechanisms or anchoring side geometries of the attachment of the molecule to the Raman-active material. In one regard, the information may be obtained because the spectrum of vibration of the molecule changes when the molecule is anchored in different respects to the Raman-active material. In other words, different anchoring mechanisms may result in different spectrums of vibration of the molecule, which the apparatus 100 may be employed to detect.

The apparatus 100 comprises an interferometer that splits the Raman scattered beam in half and selects the mutually perpendicular polarizations for each beam. After rotation of polarization of one of the split beams by 90°, the polarizations of both beams become parallel with each other. Then, the non-rotated and rotated beams are mixed together and the intensity of the recombined beam are analyzed, in which the combined beam is relatively larger when the linearly polarized split beams have the same phase and is relatively smaller when the linearly polarized split beams have different phases. By analyzing the interference pattern of the recombined beam at a required frequency, the relative phases of the non-rotated and rotated beams may be determined, that would correspond to the phase difference between cross-polarized components in the scattered beam providing that optical paths of the split beams are the same. This permits the relative phases of the components of the Raman tensor Rij to be determined. For instance, if the incident beam was y-polarized: $E^{(i)}=(0,E^{(i)}y,0)$, the beam that has been scattered in the x-direction will measure the phase difference between Ryy and Ryz components.

As shown in FIG. 1, a beam of the Raman scattered light is backscattered through the beam splitter 112 and flows through a light source rejecting filter 114 prior to being split into the first optical path 118 and the second optical path 120.

In this regard, the apparatus 100 depicted in FIG. 1 comprises a 180°-180° Raman spectrometer geometry because both of the optical paths 118 and 120 contain Raman scattered light having the same initial orientation. As discussed above, the Raman-shifted light beam 106 emitted from the light source 104 is polarized by the polarizer 108 to have a particular orientation as denoted by the arrow 109. In any regard, the light source rejecting filter 114 is to filter out the central non-Raman shifted light from being analyzed. The filtered light beam thus has a superposition of the y-component and the z-component of the Raman scattered light, but does not contain the central (not Raman shifted) line removed by notch filter.

A beam splitter 116 is depicted as splitting the filtered light beam into the first optical path 118 and the second optical path 120. The beam splitter 116 may split the filtered light beam equally between the first optical path 118 and the second optical path 120, such that, the light beams in both optical paths 118 and 120 have the same or similar intensities. As shown in FIG. 1, the second optical path 120 is relatively longer than the first optical path 118. The second optical path 120 is also depicted as including reflectors 124 and 134 to cause the light beam in the second optical path 120 to flow in the same direction as the light beam in the first optical path 118. The numbers and placements of the reflectors 124 and 134 may differ from those depicted in FIG. 1 so long as the light beam in the second optical path 120 reaches the same destination as the light beam in the first optical path 118.

The light beam in the first optical path 118 (first light beam) travels through a polarizer 122 thereby causing the light beam to have a particular orientation, denoted by the arrow (x(yy)x). In addition, the light beam in the second optical path 120 (second light beam) travels through a polarizer 126 thereby causing the light beam to have a particular polarization orientation as denoted by the arrow x(yz)x. The second light beam also goes through a polarization rotating device 130 that rotates the polarization of the second light beam to be substantially parallel to the orientation of the first light beam, as indicated by the arrow 131. The polarization rotating device 130 may be employed to rotate the polarization of the second beam into different orientations during different iterations to thereby enable a determination of various phase shifts resulting from different combinations of orientations among the first and second beams to be made.

The second light beam further goes through an optical phase modulator 132 that is to modulate/delay the phase of the second light beam with an objective to change the optical path of the second beam and, in particularly, to make it equal to the optical path of the first optical beam. The optical phase modulator 132 may comprise a crystal, such as, lithium niobate, whose refractive index is a function of the strength of a local electric field being applied on the crystal, may be based on nonlinear optical fiber, Silicon-on-Insulator (SOI) waveguides, silicon metal-oxide-semiconductor capacitor, etc. As such, the rate at which light travels through the optical phase modulator 132 may be varied by varying the electric field applied to the optical phase modulator 132. In addition, the phase of the light leaving the optical phase modulator 132 is directly proportional to the length of time the light took to pass through the optical phase modulator 132. The phase of the light beam may also be controlled by changing the electric field applied to the optical phase modulator 132. As discussed in greater detail below, the optical phase modulator 132 thus enables the phase of the second light beam to be controllably changed, which enables the shifts in phases in a combined light beam to be determined.

The apparatus 100 is further depicted as including a beam splitter 136 that combines the first light beam and the second light beam together and a spectrometer 138 to receive the combined light beams and to measure a phase shift between the first light beam and the second light beam. The spectrometer 138 is, more particular, to analyze a pattern formed by the recombined light beam at required frequency, such as, a pattern of bright and dark areas, from which the phase difference in the first and second light beams may be determined. In addition, by measuring the difference in the periodicity and position of the central peak in response to phase changes in the second light beam by the optical phase modulator 132, the phase difference between the first and second light beams may be determined. Moreover, the phase difference may be determined for each component pair in the Raman tensor, for instance, between yz and yy or between zz and zy component pairs by changing the orientations of the polarization of the incident light beam and first and second scattered light beams.

The measured phase difference between the first and second light beams corresponds to the relative phase of two components, for instance, the Ryz and the Ryy components of the Raman tensor if the optical path lengths of the first optical path 118 and the second optical path 120 are equivalent to each other. However, as shown in FIG. 1, the first optical path 118 is relatively shorter than the second optical path 120. In one regard, the optical phase modulator 132 may be employed to tune and compensate for the difference in the optical path lengths of the first and second optical paths 118 and 120. More particularly, a preliminary adjustment of the apparatus 100 may be performed to tune the first and second light beams as discussed in greater detail herein below.

Figure 2:
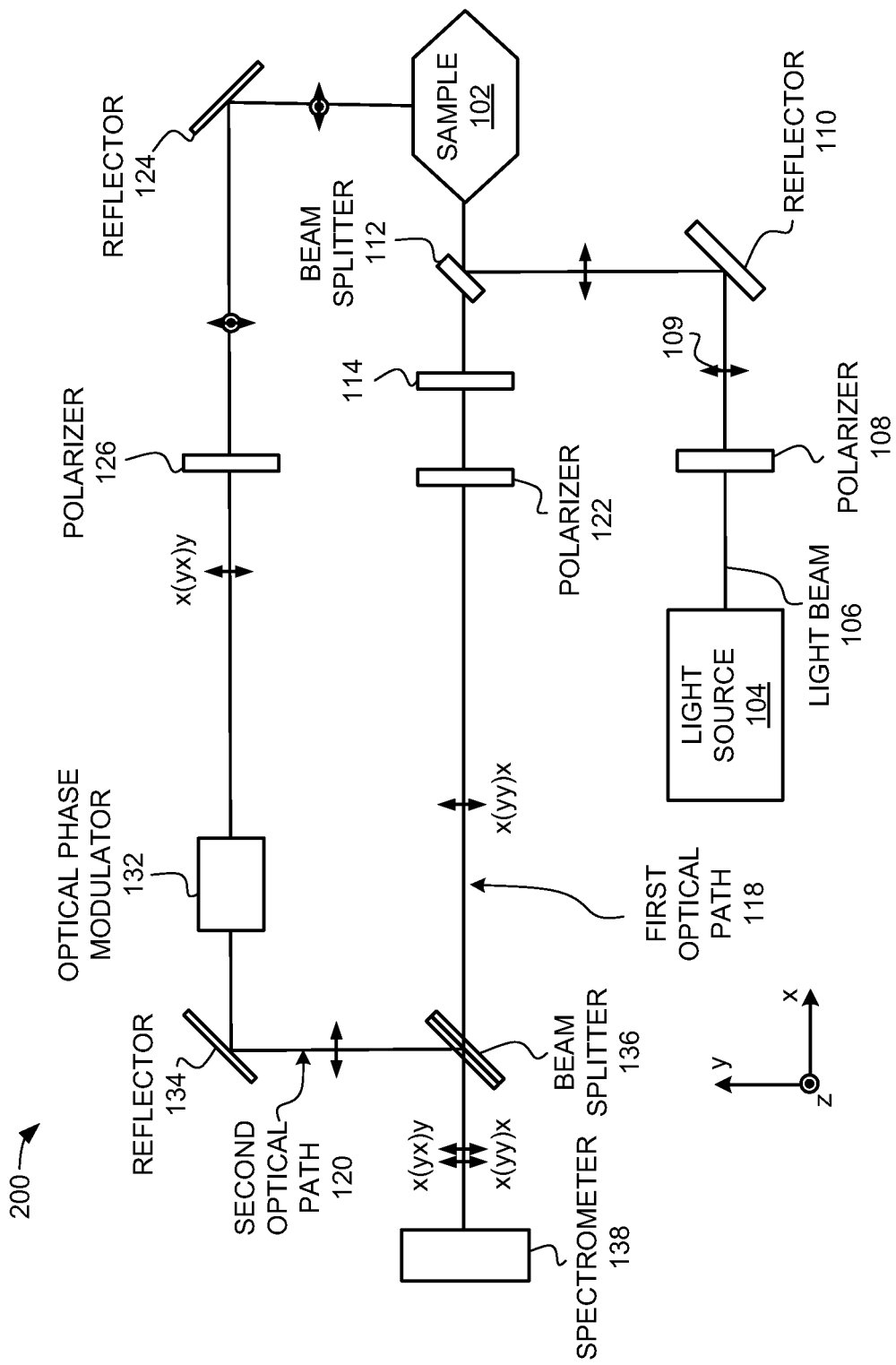
FIG. 2 shows a block diagram of an apparatus for phase detection of Raman scattered light emitted from a sample, according to another example of the present disclosure.

Turning to FIG. 2, there is shown a block diagram of an apparatus 200 for phase detection of Raman scattered light emitted from a sample 102, according to another example of the present disclosure. It should be understood that the apparatus 200 depicted in FIG. 2 may include additional components and that some of the components described herein may be removed and/or modified without departing from a scope of the apparatus 200. It should also be understood that the components depicted in FIG. 2 are not drawn to scale and thus, the components may have different relative sizes and positions with respect to each other than as shown therein.

The apparatus 200 depicted in FIG. 2 contains all of the same elements as those depicted in the apparatus 100 in FIG. 1. The apparatus 200 differs from the apparatus 100 in that the Raman beam traversing the second optical path 120 is at 90° with respect to the Raman beam traversing the first optical path 118. As such, the beam splitter 116 and the polarization rotating device 130 have been omitted from the apparatus 200. Otherwise, the descriptions of the remaining elements of the apparatus 100 in FIG. 1 are applicable to the elements of the apparatus 200 depicted in FIG. 2. As it follows from FIG. 2, depending on the orientations of polarizers 108, 122 and 126, the apparatus 200 permits the relative phase of the following pairs of the Raman tensor elements: Ryy or Rzz with Ryz, Ryx, Rzz or Rzx to be measured.

Figure 3:
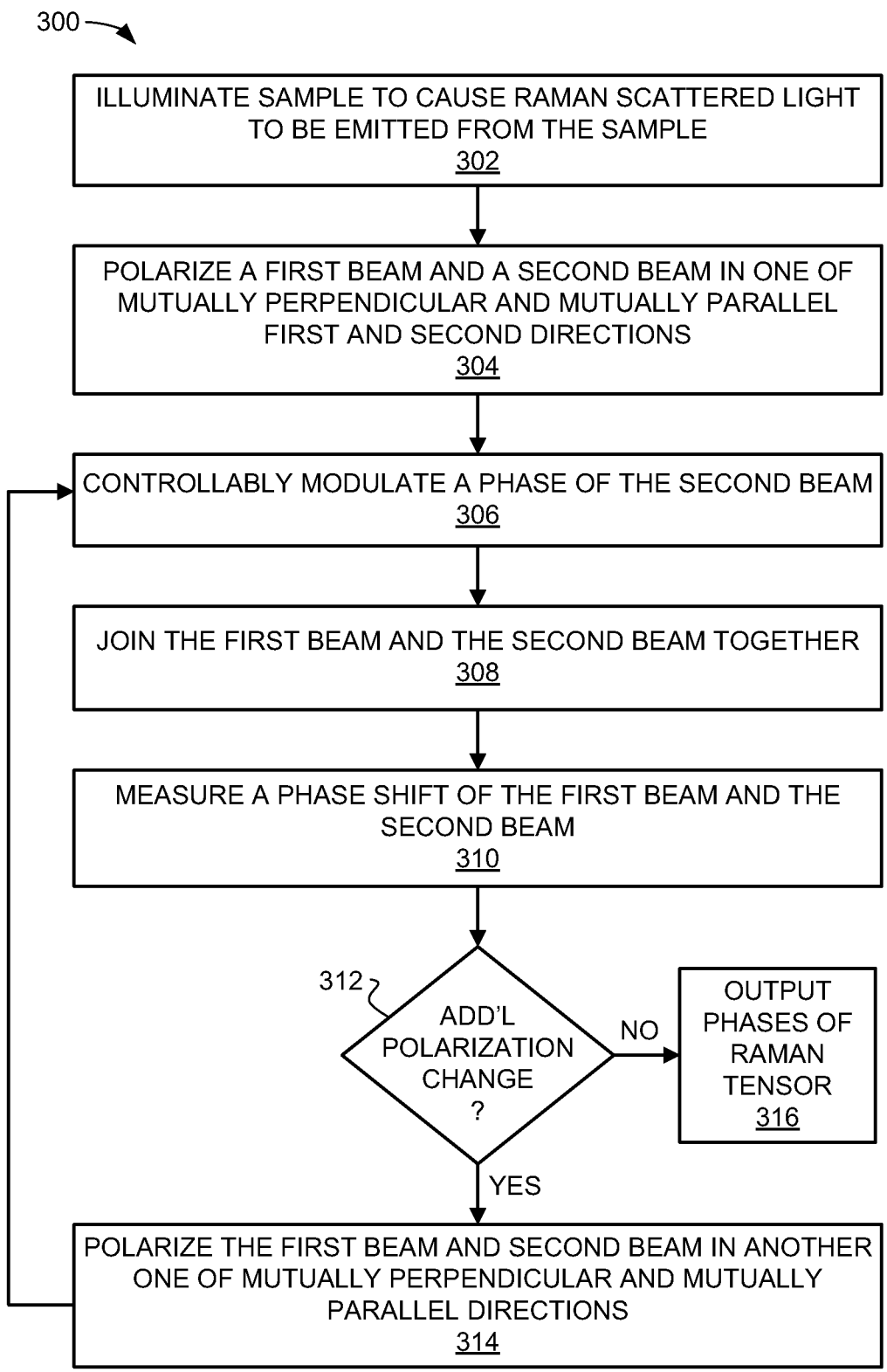
FIG. 3 shows a flow diagram of a method for phase detection of Raman scattered light emitted from a sample, according to an example of the present disclosure.

Turning now to FIG. 3, there is shown a flow diagram of a method 300 for phase detection of Raman scattered light emitted from a sample, according to an example. It should be understood that the method 300 depicted in FIG. 3 may include additional steps and that some of the steps described herein may be removed and/or modified without departing from a scope of the method 300.

The description of the method 300 is made with particular reference to the apparatuses 100 and 200 depicted in FIGS. 1 and 2. It should, however, be understood that the method 300 may be employed by apparatuses having configurations that differ from the configurations of the apparatuses 100 and 200.

At block 302, a sample 102 is illuminated to cause Raman scattered light to be emitted from the sample 102, in which the Raman scattered light forms a Raman beam having a first component, a second component, and a third component. The first component, the second component, and the third components generally comprise values that may be employed to determine the Raman tensor of the Raman scattered light. Thus, for instance, the first component comprises an intensity value of the incident and scattered light in the x-direction, the second component comprises an intensity value of the incident and scattered light in the y-direction, and the third component comprises an intensity value of the incident and scattered light in the z-direction. Each component may have two mutually perpendicular polarizations that are transversals to the light propagation direction.

In addition, the sample 102 may be illuminated by a light beam 106 from a light source 104. The light beam 106 may be polarized by a polarizer 108 prior to illuminating the sample 102, such that, the light beam 106 has a particular orientation, for instance, the x-direction. Moreover, the Raman beam emitted from the sample 102 may flow through a light source rejecting filter 114 that filters light having the particular orientation of the light beam 106 such that the Raman beam traversing the first and second optical paths 118, 120 have a superposition of, for instance, the y-polarized component and the z-polarized component of the Raman scattered light.

At block 304, a first beam of the Raman scattered light traversing a first optical path 118 and a second beam of the Raman scattered light traversing a second optical path 120 are polarized in one of mutually perpendicular and mutually parallel first and second directions. The first optical path 118 and the second optical path 120 may originate from the sample 102 in either of the configurations depicted in FIGS. 1 and 2. As shown in FIG. 1, both the first optical path 118 and the second optical path 120 originate from the sample 102 along the same axis. In this regard, the orientations of the Raman beams in the first optical path 118 and the second optical path 120 are initially identical prior to being split by the beam splitter 116. The polarizers 122 and 126 polarize the Raman beams to be mutually perpendicular to each other. In addition, the polarization rotating device 130 positioned along the second optical path 120 rotates the polarization of the second beam and causes the orientation of the second beam to be substantially parallel to the orientation of the first beam.

As shown in FIG. 2, however, the first optical path 118 and the second optical path 120 originate from the sample 102 along different axes. In this regard, the orientations of the Raman beams in the first optical path 118 and the second optical path 120 are initially different from each other. In this regard, the polarizers 122, 126 may polarize the Raman beams to be mutually parallel to each other and the light source rejecting filter 114 filters light along the first optical path 118.

At block 306, a phase of the second beam traversing the second optical path 120 is controllably modulated by the optical phase modulator 132. By way of example, the optical phase modulator 132 is operated to modulate the phase of the second beam to compensate for the difference in the optical path lengths of the first and second optical paths 118 and 120.

At block 308, the first beam and the second beam are joined together by the beam splitter 136. In addition, the combined beams are directed onto the spectrometer 138.

At block 310, the spectrometer 138 measures a phase shift between the first beam and second beam. More particularly, for instance, the spectrometer 138 determines an interference pattern of the combined beam and based upon the interference pattern, the spectrometer 138 may determine the phase difference between the first and second beams. By way of example, the spectrometer 138 may determine that the y-polarized component and z-polarized component of the Raman tensor are in-phase when the intensity of the recombined beam is larger whereas they are out-of-phase when the intensity of the recombined beam is smaller.

At block 312, a determination as to whether additional phases of the Raman tensor elements are to be determined is made. In response to a determination that additional phases of the Raman tensor elements are to be determined, the polarization of the first beam and the second beam may be varied to therefore cause the orientations of the first beam and the second beam to be in another one of mutually perpendicular and mutually parallel directions, as indicated at block 314. In this regard, either or both of the first and second beams may have different orientations as compared with their orientations following block 304. In addition, blocks 306-312 may be performed using the first and second beams at the orientations resulting at block 314 to measure the phase shift of the first and second beams. Blocks 306-314 may be repeated for a number of iterations to determine the phases of each of the Raman tensor elements. Thus, for instance, blocks 306-314 may be repeated with different combinations of the first beam and the second beam orientations (yy, yz, zz, etc.) to determine the phase shifts between the different components of the Raman tensor.

In response to a determination that no additional phases of the Raman tensor components are to be determined at block 312, the phases of the Raman tensor components are outputted at block 316. The phases of the Raman tensor components may be outputted for analysis by a computing device and/or a human operator. In addition, although not explicitly depicted in FIG. 3, the absolute values of the Raman tensor components may also be measured at block 310 and outputted at block 316.

Figure 4:
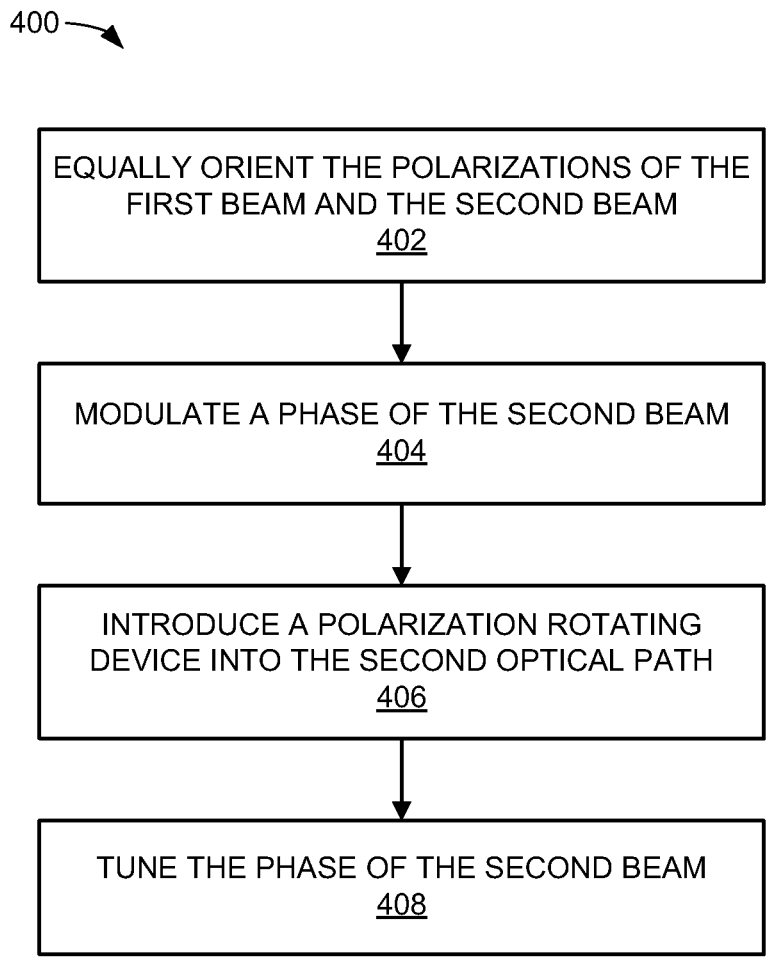
FIG. 4 shows a flow diagram of a method for preliminarily adjusting the apparatuses depicted in FIGS. 1 and 2, according to an example of the present disclosure.

With reference now to FIG. 4, there is shown a flow diagram of a method 400 for preliminarily adjusting the apparatuses 100, 200 depicted in FIGS. 1 and 2, according to an example. It should be understood that the method 400 depicted in FIG. 4 may include additional steps and that some of the steps described herein may be removed and/or modified without departing from a scope of the method 400.

At block 402, the polarizations of the first beam and the second beam are equally oriented with respect to each other. For instance, the first beam and the second beam may be oriented along the z-direction, such that the first light beam and the second light beam are provided by the same Rxz component of the Raman tensor. At block 404, the optical phase modulator 132 is modulated to cause a constructive interference to occur between the first and second light beams for any wavelength of the Raman scattered light and to therefore ensure an equal optical path length between the first and second optical paths 118 and 120.

With respect to the apparatus 100 depicted in FIG. 1, at block 406, the polarization rotating device 130 is introduced back into the apparatus 100. In addition, at block 408, the optical phase modulator 132 is further tuned to compensate for the inclusion of the polarization rotating device 130 into the second optical path 120.

Following the adjustment described with respect to the method 400, the spectrometer 138 is able to directly measure the relative phase of the components of the Raman tensor, such as, the Ryy and the Ryz components, as discussed above.

Figure 5:
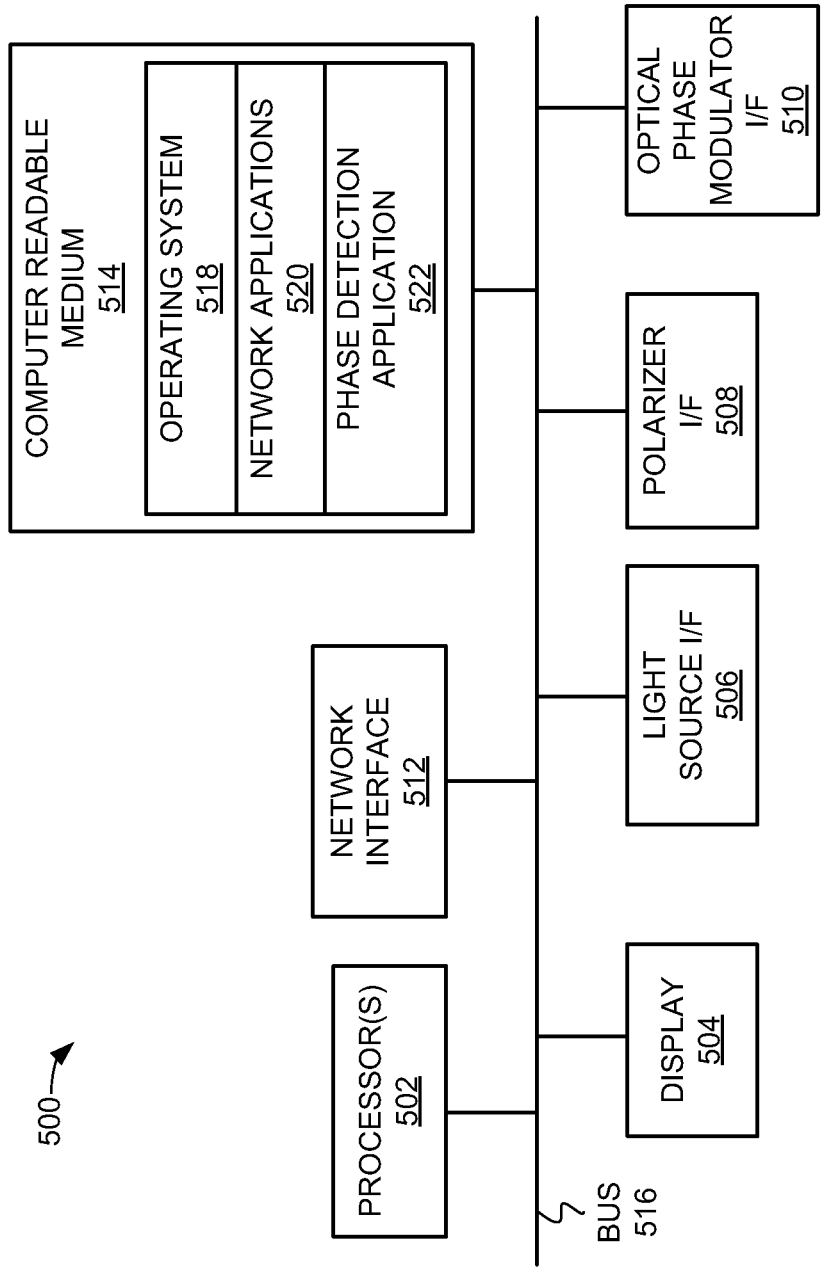
FIG. 5 shows a schematic representation of a computing device configured to implement the methods depicted in FIGS. 3 and 4, according to an example of the present disclosure.

Turning now to FIG. 5, there is shown a schematic representation of a computing device 500 configured to implement or execute the methods 300 and 400, in accordance with an example of the present disclosure. The computing device 500 may comprise, for instance, a desktop computer, laptop, server, etc. The computing device 500 includes a processor 502, such as a central processing unit; a display device 504, such as a monitor; a light source interface (I/F) 506; a polarizer interface 508; an optical phase modulator interface 510; a network interface 512, such as a Local Area Network LAN, a wireless 802.11x LAN, a 3G mobile WAN or a WiMax WAN; and one or more computer-readable mediums 514. Each of these components is operatively coupled to a bus 516. For example, the bus 516 may be an EISA, a PCI, a USB, a FireWire, a NuBus, or a PDS.

The computer readable medium 514 may be any suitable medium that participates in providing instructions to the processor 502 for execution. For example, the computer readable medium 510 may be non-volatile media, such as an optical or a magnetic disk; volatile media, such as memory; and transmission media, such as coaxial cables, copper wire, and fiber optics. Transmission media can also take the form of acoustic, light, or radio frequency waves.

The computer-readable medium 510 may also store an operating system 518, such as Mac OS, MS Windows, Unix, or Linux; network applications 520; and a phase detection application 522. The operating system 518 may be multi-user, multiprocessing, multitasking, multithreading, real-time and the like. The operating system 518 may also perform basic tasks such as recognizing input from input devices, such as a keyboard or a keypad; sending output to the display 504, the light source 104, the polarizers 122, 126, and the optical phase modulator 132; keeping track of files and directories on medium 514; controlling peripheral devices, such as disk drives, printers, image capture device; and managing traffic on the bus 516. The network applications 520 include various components for establishing and maintaining network connections, such as software for implementing communication protocols including TCP/IP, HTTP, Ethernet, USB, and FireWire.

The phase detection application 522 provides various software components for detecting the phases of components of a Raman tensor, as described above. In certain examples, some or all of the processes performed by the phase detection application 522 may be integrated into the operating system 518. In certain examples, the processes may be at least partially implemented in digital electronic circuitry, or in computer hardware, firmware, software, or in any combination thereof.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for phase detection of Raman scattered light emitted from a sample, said apparatus comprising:
   a first polarizer positioned along a first optical path containing a first beam of the Raman scattered light and a second polarizer positioned along a second optical path containing a second beam of the Raman scattered light, said first polarizer and second polarizer to polarize the first beam and the second beam in one of mutually perpendicular and mutually parallel first and second directions;
   an optical phase modulator positioned along the second optical path, wherein the optical phase modulator is to controllably modulate a phase of the second beam;
   a beam splitter positioned to join the first beam and the second beam together; and
   a spectrometer to receive the joined first beam and second beam and to measure a phase shift of the first beam and the second beam.

2. The apparatus according to claim 1, wherein the Raman scattered light has a first component, a second component, and a third component, said apparatus further comprising:
   a light source rejecting filter positioned to filter light from the Raman scattered light along a third component direction thereby causing the Raman scattered light emitted through the light source rejecting filter to comprise a Raman beam having a superposition of the first component and the second component of the Raman scattered light.

3. The apparatus according to claim 2, further comprising:
   a light source to emit a light beam on the sample to cause the Raman scattered light to be emitted from the sample; and
   a third polarizer to polarize the light beam to be emitted onto the sample in the third component direction.

4. The apparatus according to claim 1, further comprising:
   a polarization rotating device positioned along the second optical path to rotate the polarization of the second beam and cause the orientation of the second beam to be substantially parallel to the orientation of the first beam prior to being joined with the first beam.

5. The apparatus according to claim 1, wherein the optical phase modulator is to be tuned to compensate for a difference in optical path lengths of the first optical path and the second optical path.

6. The apparatus according to claim 1, wherein the joining of the first beam and the second beam results in an interference, and wherein the spectrometer is to measure a phase shift of the first beam and the second beam from the interference.

7. The apparatus according to claim 6, wherein the spectrometer is to measure a phase shift of zero in response to the interference being constructive and pi in response to the interference being destructive.

8. The apparatus according to claim 1, wherein the spectrometer is to determine phases of a tensor of the Raman scattered light.

9. A method for phase detection of Raman scattered light emitted from a sample, said method comprising:
   illuminating the sample to cause Raman scattered light to be emitted from the sample, the Raman scattered light forming a Raman beam having a first component, a second component, and a third component;
   polarizing a first beam of the Raman scattered light traversing a first optical path and a second beam of the Raman scattered light traversing a second optical path in one of mutually perpendicular and mutually parallel first and second directions;
   controllably modulating a phase of the second beam;
   joining the first beam and the second beam together; and
   measuring a phase shift of the first beam and the second beam from the joined first beam and the second beam.

10. The method according to claim 9, further comprising:
    illuminating the sample with a light beam that is polarized in a third component direction;
    filtering light from the Raman scattered light along the third component direction to filter light from the light beam thereby causing the Raman scattered light to comprise a Raman beam having a superposition of the first component and the second component of the Raman scattered light.

11. The method according to claim 9, further comprising:
rotating the polarization of the second beam to cause the orientation of the second beam to be substantially parallel to the orientation of the first beam.

12. The method according to claim 9, further comprising:
determining phases of a tensor of the Raman scattered light from the measured phase shift.

13. The method according to claim 9, further comprising:
polarizing the first beam and the second beam in another one of mutually perpendicular and mutually parallel directions;
controllably modulating a phase of the second beam;
joining the first beam and the second beam together; and
measuring a phase shift of the first beam and the second beam from the joined first beam and the second beam.

14. The method according to claim 9, wherein the first beam traverses a first optical path and the second beam traverses a second optical path, and wherein the second optical path is relatively longer than the first optical path, said method further comprising:
performing a preliminary adjustment by,
equally orienting the polarization of the first beam and the second beam; and
modulating a phase of the second beam to make the optical path lengths of the first optical path and the second optical path to be substantially the same.

15. An apparatus for performing surface enhanced Raman spectroscopy (SERS), said apparatus comprising:
a first polarizer positioned along a first optical path containing a first beam of the surface enhanced Raman scattered light from a sample and a second polarizer positioned along a second optical path containing a second beam of the surface enhanced Raman scattered light, said first polarizer and second polarizer to polarize the first beam and the second beam in one of mutually perpendicular and mutually parallel first and second directions;
an optical phase modulator positioned along the second optical path, wherein the optical phase modulator is to controllably modulate a phase of the second beam;
a beam splitter positioned to join the first beam and the second beam together; and
a spectrometer to receive the joined first beam and second beam and to measure a phase shift of the first beam and the second beam.

* * * * *